United States Patent [19]

Henning et al.

[11] Patent Number: 4,912,128
[45] Date of Patent: Mar. 27, 1990

[54] NOVEL PYRROLIDINE-2-(1,3-DICARBONYL) DERIVATIVES, A PROCESS FOR THEIR PREPARATION, AGENTS CONTAINING THEM, AND THEIR USE

[75] Inventors: Rainer Henning, Hattersheim am Main; Franz Hock, Dieburg; Hansjörg Urbach, Kronbert, all of Fed. Rep. of Germany

[73] Assignee: Hoechst Aktiengesellschaft, Frankfurt am Main, Fed. Rep. of Germany

[21] Appl. No.: 179,312

[22] Filed: Apr. 8, 1988

[30] Foreign Application Priority Data

Apr. 11, 1987 [DE] Fed. Rep. of Germany ....... 3712364

[51] Int. Cl.$^4$ ............... C07D 207/09; C07D 207/12; A61K 31/40
[52] U.S. Cl. ................................. 514/422; 530/330; 530/331; 546/281; 548/518; 548/526; 548/527; 548/536; 548/537; 548/538; 548/540; 544/372
[58] Field of Search ............... 260/998.2; 530/331; 548/518, 530, 531, 532, 533, 535, 536, 537, 538, 540; 514/422

[56] References Cited

U.S. PATENT DOCUMENTS

| | | | |
|---|---|---|---|
| 4,077,951 | 3/1978 | Loffet | 548/518 |
| 4,277,395 | 7/1981 | Bey et al. | 548/537 X |
| 4,439,619 | 3/1984 | Bey et al. | 260/998.2 X |
| 4,456,594 | 6/1984 | Pfeiffer | 548/518 X |
| 4,483,991 | 11/1984 | Freed | 548/518 X |
| 4,499,102 | 2/1985 | Oya et al. | 548/533 X |
| 4,518,528 | 5/1985 | Rasnic | 548/533 |
| 4,560,795 | 12/1985 | Bey et al. | 260/998.2 X |
| 4,719,200 | 1/1988 | Eguchi et al. | 530/331 X |
| 4,720,554 | 1/1988 | Irie et al. | 548/533 |
| 4,762,821 | 8/1988 | Nestor | 548/538 X |

FOREIGN PATENT DOCUMENTS 0268281  5/1988  European Pat. Off. ............ 548/518

*Primary Examiner*—Joseph Paul Brush
*Attorney, Agent, or Firm*—Finnegan, Henderson, Farabow, Garrett and Dunner

[57] ABSTRACT

Novel pyrrolidine-2-(1,3-dicarbonyl) derivatives, a process for their preparation, agents containing them, and their use The invention relates to pyrrolidine derivatives of the general formula

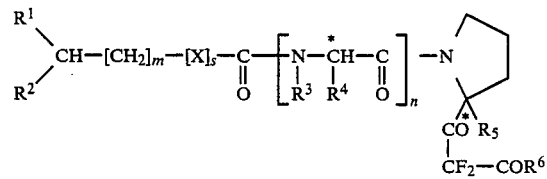

in which
$R^1$, $R^2$, $R^3$, $R^4$, $R^5$ and $R^6$ have the meaning specified in the description, X denotes oxygen, imino or alkylimino,
m is 0–5, n is 0–2 and s is 0 or 1, a process for their preparation, agents containing them, and their use.

19 Claims, No Drawings

NOVEL PYRROLIDINE-2-(1,3-DICARBONYL) DERIVATIVES, A PROCESS FOR THEIR PREPARATION, AGENTS CONTAINING THEM, AND THEIR USE

DESCRIPTION

The invention relates to pyrrolidine derivatives of the general formula I

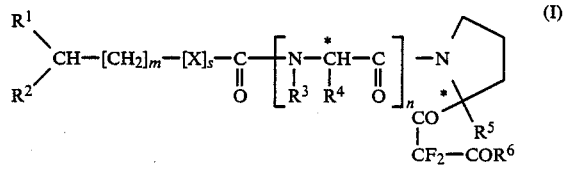

in which $R^1$ denotes hydrogen; $(C_1-C_6)$-alkyl or $(C_6-C_{12})$-aryl which is optionally substituted by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or one ($C_1$ or $C_2$)-alkylenedioxy;

$R^2$ denotes hydrogen; $(C_1-C_6)$-alkyl; $(C_6-C_{12})$-aryl; $(C_6-C_{12})$-aryloxy; $(C_7-C_{13})$-aroyl, hydroxyl or $(C_1-C_4)$-alkoxy, where aryl, aryloxy and aroyl are in each case optionally substituted by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or by one ($C_1$ or $C_2$)-alkylenedioxy; or $R^1$ and $R^2$ together represent benzylidene in which the phenyl ring is optionally substituted by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or by one ($C_1$ or $C_2$)-alkylenedioxy;

$R^3$ denotes hydrogen; $(C_1-C_6)$-alkyl; $(C_6-C_{12})$-aryl-$(C_1-C_6)$-alkyl; $(C_5-C_9)$-cycloalkyl; indanyl or tetrahydronaphthyl;

$R^4$ denotes hydrogen; $(C_1-C_6)$-alkyl which may optionally be monosubstituted by amino, $(C_1-C_6)$-acylamino, in particular $(C_1-C_6)$-alkanoylamino or Boc-NH, or benzoylamino; $(C_2-C_6)$-alkenyl; $(C_5-C_9)$-cycloalkyl; $(C_5-C_9)$ cycloalkenyl; $(C_5-C_7)$-cycloalkyl-$(C_1-C_4)$-alkyl; $(C_6-C_{12})$-aryl or partly hydrogenated $(C_6-C_{12})$-aryl which may in each case be substituted by one, two or three identical or different radicals from the series comprising $(C_1-C_4)$-alkyl, $(C_1-C_2)$-alkoxy and halogen; $(C_6-C_{12})$-aryl-$(C_1-C_4)$-alkyl or $(C_7-C_{13})$-aroyl-$(C_1$ or $C_2)$-alkyl which may both be substituted in the aryl radical as defined above; a mono- or bicyclic heterocyclic radical having 5 to 7 or 8 to 10 ring atoms respectively, of which 1-9 ring atoms are carbon atoms and 1 or 2 ring atoms are sulfur or oxygen atoms and/or of which 1 to 4 ring atoms are nitrogen atoms, or, if not yet covered by the definitions above, the optionally protected side chain of a naturally occurring α-amino acid; or $R^3$ and $R^4$ together represent —$[CH_2]_p$— in which p is 3, 4 or 5 and in which one methylene group may be replaced by S or O;

$R^5$ denotes hydrogen; $(C_1-C_6)$-alkyl; $(C_6-C_{12})$-aryl-$(C_1-C_5)$-alkyl which is optionally substituted in the aryl part by one, two or three identical or different radicals from the series comprising $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or by one ($C_1$ or $C_2$)-alkylenedioxy;

$R^6$ denotes $(C_1-C_8)$-alkyl; $(C_6-C_{12})$-aryl; $(C_6-C_{12})$-aryl-$(C_1-C_6)$-alkyl; hydroxyl; $(C_1-C_8)$-alkoxy; $(C_6-C_{12})$-aryloxy or $(C_6-C_{12})$-aryl-$(C_1-C_6)$-alkoxy, where aryl, aralkyl, aryloxy and arylalkoxy may in each case be substituted in the aryl part by one, two or three identical or different radicals from the series comprising $(C_1-C_4)$-alkyl, ($C_1$ or $C_2$)-alkoxy, halogen and nitro, or by one ($C_1$ or $C_2$)-alkylenedioxy; or $R^6$ represents a radical of the formula —$NR^7R^8$;

$R^7$ and $R^8$ are identical or different and denote hydrogen; $(C_1-C_8)$-alkyl; $(C_4-C_{10})$-cycloalkyl; $(C_1-C_4)$-alkyl-$(C_4-C_{10})$-cycloalkyl; $(C_6-C_{12})$-aryl; $(C_6-C_{12})$-aryl-$(C_1-C_6)$-alkyl; 2-, 3- or 4-pyridyl-$(C_1-C_4)$-alkyl; amino-$(C_1-C_8)$-alkyl; $(C_1-C_4)$-alkylamino-$(C_1-C_8)$-alkyl; di-$(C_1-C_4)$-alkylamino-$(C_1-C_8)$-alkyl; hydroxy-$(C_1-C_8)$-alkyl or $(C_1-C_4)$-alkoxy-$(C_1-C_8)$-alkyl, where aryl and aralkyl may in each case be substituted in the aryl part by one, two or three identical or different radicals from the series comprising $(C_1-C_4)$-alkyl, ($C_1$ or $C_2$)-alkoxy, $(C_1-C_4)$-alkylamino, di-$(C_1-C_4)$-alkylamino, halogen, hydroxyl and amino, or by one ($C_1$ or $C_2$)-alkylenedioxy; or $R^7$ and $R^8$, together with the nitrogen atom carrying them, form a 4- to 12-membered, saturated or partly unsaturated mono- or bicyclic heterocyclic ring which contains as ring atoms 2–11 carbon atoms and optionally 1 or 2 further identical or different heteroatoms from the series comprising oxygen, sulfur and nitrogen, and which is optionally substituted by a radical from the series comprising $(C_1-C_8)$-alkyl, phenyl, phenyl-$(C_1-C_6)$-alkyl, benzoyl, phenyl-$(C_2-C_4)$-alkanoyl, 2- or 3-furoyl, 2-, 3- or 4-pyridyl and 2-, 4- or 5-pyrimidinyl, where phenyl, phenylalkyl, benzoyl and phenylalkanoyl may themselves in each case be substituted in the phenyl part by one, two or three identical or different radicals from the series comprising $(C_1-C_4)$-alkyl, ($C_1$ or $C_2$)-alkoxy, halogen and nitro, or by one ($C_1$ or $C_2$)-alkylenedioxy;

X denotes oxygen; imino or N-$(C_1-C_8)$-alkylimino;

m is 0, 1, 2, 3, 4 or 5;

n is 0, 1 or 2, and s is 0 or 1, and their physiologically acceptable salts, if it is possible for these to be formed.

Alkyl may be straight-chain or branched and is, for example, methyl, ethyl, propyl, isopropyl, butyl, isobutyl, sec.-butyl, tert.-butyl, pentyl, isopentyl, neopentyl, sec.-pentyl, tert.-pentyl, hexyl, isohexyl, heptyl or octyl. The equivalent applies to radicals derived therefrom, such as alkoxy, alkylamino, dialkylamino, alkanoyl, alkoxycarbonyl and aralkyl.

Aryl is, for example, phenyl, α- or β-naphthyl, or 2-, 3- or 4-biphenyl; phenyl is preferred. The equivalent applies to radicals derived therefrom, such as aryloxy, aralkyl, aryl, aroyl and arylalkanoyl.

Halogen is fluorine, chlorine, bromine or iodine; fluorine, chlorine and bromine are preferred.

Where $R^4$ is a mono- or bicyclic heterocyclic radical having 5 to 7 or 8 to 10 ring atoms respectively, of which 1 to 9 ring atoms are carbon atoms and 1 to 2 ring atoms are sulfur or oxygen atoms and/or of which 1 to 4 ring atoms are nitrogen atoms, this is taken to mean, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals may also be partly or completely hydrogenated.

Compounds of the formula I have asymmetrical carbon atoms. Both the R and S configurations at all centers of asymmetry are subject-matter of the invention. The compounds of the formula I can therefore exist as optical isomers, as diasteromers, as racemates or as mixtures thereof. However, compounds of the formula I in which the carbon atoms labelled with an asterisk (*) have the S configuration are preferred. However, if $R^4$ represents the side chain of cystein, the R configuration of this center is preferred.

Naturally occurring α-amino acids, such as, for example, Ala, Val, Leu, Ile, Phe, Abu, C-Ph-Gly, His, Trp, Lys, Orn, Dab, Dap, Daap, Dapi, Arg, Cit, Glu, Gln, Asp, Asu, Cys, Met, Hyl, Ser, Thr and Tyr, are described, for example, in Ann. Rev. Biochem. 38 [1969] 137-158 and FEBS Letters 64 [1976] 29-35.

If $R^4$ represents a protected side chain of a naturally occurring α-amino acid, such as, for example, protected Ser, Thr, Asp, Asn, Glu, Gln, Arg, Lys, Hyl, Cys, Orn, Cit, Tyr, Trp or His, preferred protective groups are the groups which are conventional in peptide chemistry (cf., for example, T. W. Greene, "Protective Groups in Organic Synthesis", N.Y., 1981 or Bodanszky, Bodanszky, "Principles and Practice of Peptide Synthesis", Berlin, 1984). In the case where $R^4$ denotes a protected lysine side chain, the known amino-protecting groups, but in particular $(C_1–C_6)$-alkanoyl, are preferred. If $R^4$ denotes a protected tyrosine side chain, the ether-protecting group on oxygen, in particular $(C_1–C_6)$-alkyl, is preferred; particularly preferred protecting groups are methyl and ethyl.

Suitable salts are, in particular, alkali metal or alkaline-earth metal salts, salts with physiologically acceptable amines and salts with inorganic or organic acids, such as, for example, HCl, HBr, $H_2SO_4$, maleic acid and fumaric acid.

Preferred compounds of the formula I are those in which $R^1$ denotes hydrogen; $(C_1–C_4)$-alkyl or phenyl which is optionally substituted by one or two identical or different radicals from the series comprising methyl, ethyl, methoxy, fluorine, chlorine, bromine, nitro, hydroxyl, amino, methylamino and dimethylamino, or by three methoxy, or by one methylenedioxy;

$R^2$ denotes hydrogen; phenyl; phenoxy; benzoyl; hydroxyl or methoxy, where phenyl, phenoxy and benzoyl are in each case optionally substituted by one or two identical or different radicals from the series comprising methyl, ethyl, fluorine, chlorine, bromine, nitro, hydroxyl, amino, methylamino and dimethylamino, or by one methylenedioxy; or $R^1$ and $R^2$ together represent benzylidene in which the phenyl radical is optionally substituted by one or two identical or different radicals from the series comprising methyl, ethyl, methoxy, fluorine, chlorine, bromine and hydroxyl, by three methoxy, or by one methylenedioxy;

$R^3$ denotes hydrogen; $(C_1–C_4)$-alkyl; benzyl; phenethyl; cyclopentyl; cyclohexyl or indanyl;

$R^4$ denotes hydrogen or the optionally protected side chain of a naturally occurring α-amino acid; or $R^3$ and $R^4$ together represent a $—[CH_2]_p—$ radical as defined above and in which p is 3 or 4;

$R^5$ denotes hydrogen; methyl; ethyl; benzyl or phenethyl which is in each case optionally substituted in the phenyl radical by one, two or three identical or different radicals from the series comprising methoxy, fluorine, chlorine and bromine, or by one methylenedioxy;

$R^6$ denotes $(C_1–C_5)$-alkoxy; phenoxy; phenyl-$(C_1–C_4)$-alkoxy or hydroxyl, where phenoxy and phenylalkoxy may in each case be substituted in the phenyl radical by one or two identical or different radicals from the series comprising methyl, ethyl, methoxy, fluorine, chlorine and bromine, or by one methylenedioxy; or $R^6$ represents a radical of the formula $—NR^7R^8$ in which $R^7$ and $R^8$ are identical or different and denote hydrogen; $(C_1–C_6)$-alkyl; $(C_5–C_8)$-cycloalkyl; $(C_1$ or $C_2)$-alkyl-$(C_5–C_8)$-cycloalkyl; phenyl; phenyl-$(C_1–C_4)$-alkyl; 2-, 3- or 4-pyridyl-$(C_1–C_4)$-alkyl; amino-$(C_1–C_4)$-alkyl; $(C_1$ or $C_2)$-alkylamino-$(C_1–C_4)$-alkyl; di-$(C_1$ or $C_2)$-alkylamino-$(C_1–C_4)$-alkyl; hydroxy-$(C_1–C_4)$-alkyl or $(C_1$ or $C_2)$-alkoxy-$(C_1–C_4)$-alkyl, in which phenyl and phenylalkyl may in each case be substituted in the phenyl part by one or two identical or different radicals from the series comprising methyl, ethyl, methoxy, fluorine, chlorine, bromine, amino, methylamino and dimethylamino, or by one methylenedioxy; or $R^7$ and $R^8$, together with the nitrogen atom carrying them, form a 5- to 9-membered heterocyclic ring which contains as ring atoms 3–8 carbon atoms and optionally a further nitrogen atom or an oxygen atom and which is optionally monosubstituted by $(C_1–C_4)$-alkyl, phenyl, phenyl-$(C_1–C_4)$-alkyl, benzoyl, phenyl-$(C_2$ or $C_3)$-alkanoyl, 2- or 3-furoyl, 2-, 3- or 4-pyridyl or 2-, 4- or 5-pyrimidinyl, where phenyl, phenylalkyl, benzoyl and phenylalkanoyl may themselves in each case be substituted in the phenyl part by one or two identical or different radicals from the series comprising methyl, ethyl, methoxy, fluorine, chlorine and bromine, or by one methylenedioxy;

X denotes oxygen;

m is 0, 1, 2, 3, 4 or 5;

n is 0 or 1, and s is 0 or 1.

Particularly preferred compounds of the formula I are those in which $R^1$ denotes hydrogen; methyl; ethyl; propyl; isopropyl; phenyl; o-, m- or p-tolyl; o-, m- or p-chlorophenyl; o-, m- or p-fluorophenyl; o-, m- or p-methoxyphenyl or 2,3-, 2,4-, 2,5-, 2,6-, 3,4- or 3,5-dimethoxyphenyl;

$R^2$ denotes hydrogen; phenyl; o-, m- or p-tolyl; o-, m- or p-chlorophenyl; o-, m- or p-fluorophenyl; o-, m- or p-methoxyphenyl; 2,3-, 2,4-, 2,5-, 2,6-, 3,4- or 3,5-dimethoxyphenyl; phenoxy; o-, m- or p-tolyloxy; o-, m- or p-chlorophenoxy; o-, m- or p-fluorophenoxy; o-, m- or p-methoxyphenoxy; 2,3-, 2,4-, 2,5-, 2,6-, 3,4- or 3,5-dimethoxyphenoxy; benzoyl; o-, m- or p-toluoyl; o-, m- or p-chlorobenzoyl; o-, m- or p-fluorobenzoyl; o-, m- or p-methoxybenzoyl; 2,3-, 2,4-, 2,5-, 2,6-, 3,4- or 3,5-dimethoxybenzoyl; hydroxyl or methoxy; or $R^1$ and $R^2$ together represent benzylidene; o-, m- or p-methylbenzylidene; o-, m- or p-methoxybenzylidene or 2,3-, 2,4-, 2,5-, 2,6-, 3,4- or 3,5-dimethoxybenzylidene;

$R^3$ denotes hydrogen or methyl;

$R^4$ denotes hydrogen; methyl; n-propyl; isopropyl; n-butyl; isobutyl; sec-butyl or benzyl; or $R^3$ and $R^4$ together represent —[CH$_2$]$_3$—;

$R^5$ denotes hydrogen or methyl;

$R^6$ denotes methoxy; ethoxy; propoxy; isopropoxy; tert.-butoxy; n-butoxy; benzyloxy; 4-methoxybenzyloxy; 4-chlorobenzyloxy; 3,4-dimethoxybenzyloxy; phenethyloxy or a radical of the formula —NR$^7$R$^8$;

$R^7$ and $R^8$ are identical or different and denote hydrogen; (C$_1$–C$_6$)-alkyl; (C$_5$–C$_8$)-cycloalkyl; phenyl; phenyl-(C$_1$–C$_4$)-alkyl; 2-, 3- or 4-pyridylmethyl; 2-, 3- or 4-pyridylethyl; amino-(C$_1$–C$_4$)-alkyl; methylamino-(C$_1$–C$_4$)-alkyl; dimethylamino-(C$_1$–C$_4$)-alkyl; hydroxy-(C$_1$–C$_4$)-alkyl or methoxy-(C$_1$–C$_4$)-alkyl, where phenyl and phenylalkyl may in each case be substituted in the phenyl radical by one or two identical or different radicals from the series comprising methyl, methoxy, fluorine, chlorine, bromine, amino, methylamino and dimethylamino, or by one methylenedioxy; or $R^7$ and $R^8$, together with the nitrogen atom carrying them, represent pyrrolidino, piperidino, tetrahydropyridino, morpholino, azepino, N,N-heptamethylenimino, piperazino or homopiperazino, where the heterocyclic radicals mentioned may be monosubstituted by (C$_1$–C$_4$)-alkyl, phenyl, phenyl-(C$_1$–C$_4$)-alkyl, benzoyl, phenyl-(C$_2$ or C$_3$)-alkanoyl or 2-, 3- or 4-pyridyl, and in which phenyl, phenylalkyl, benzoyl and phenylalkanoyl may themselves be substituted in the phenyl part by one or two identical or different radicals from the series comprising methyl, methoxy, fluorine, chlorine or bromine;

X denotes oxygen;

m is 0, 1, 2, 3, 4 or 5;

n is 0 or 1, and s is 0 or 1.

Especially preferred compounds of the formula I are those in which $R^2$ denotes hydrogen;

$R^3$ and $R^4$ together represent —[CH$_2$]$_3$—;

$R^5$ denotes hydrogen;

X denotes oxygen;

m is 1, 2, 3 or 4;

n is 1, and s is 0 or 1;

and also compounds of the formula I in which $R^5$ denotes hydrogen;

X denotes oxygen;

m is 1, 2, 3 or 4;

n is 0, and s is 0 or 1.

The invention also relates to a process for the preparation of compounds of the formula I, wherein a compound of the formula IV

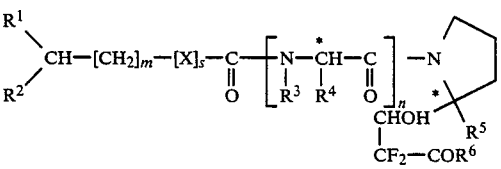

in which $R^1$, $R^2$, $R^3$, $R^4$, $R^5$ and $R^6$, X, m, n and s have the same meaning as in formula I, is oxidized, and the compound thus obtained is converted, if desired, into its physiologically acceptable salts.

The following oxidants are possible in this reaction; manganese dioxide, sodium dichromate or potassium dichromate; Jones reagent (CrO$_3$ in aqueous sulfuric acid), N-bromoacetamide, N-bromosuccinimide, dimethyl sulfoxide, cerium ammonium nitrate, CrO$_3$ in pyridine, tert.-butyl chromate, dipyridine-CrO$_3$, potassium hypochlorite or iodosobenzene. Suitable reaction media are petroleum ether, benzene, carbon tetrachloride or, in the case of MnO$_2$, dilute sulfuric acid. The oxidation is carried out between 0° C. and the boiling point of the reaction mixture. Oxidation using dimethyl sulfoxide with various additives, as described, for example, Houben-Weyl, Volume E 3, pages 275–281, is preferred. Dimethyl sulfoxide oxidation in the presence of oxalyl chloride and the process described in J. Org. Chem. 48 [1983] 4155 are especially preferred.

Compounds of the formula IV are prepared, for example, by reacting a compound of the formula II

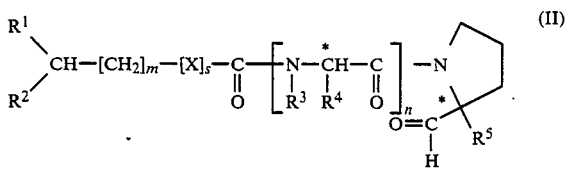

in which $R^1$, $R^2$, $R^3$, $R^4$, $R^5$, X, m, n and s have the same meaning as in formula I, with a compound of the formula III

in which $R^6$ has the same meaning as in formula I and Y denotes halogen, preferably chlorine, bromine or iodine, in an inert solvent such as an ether, dimethylformamide, diethylformamide, N-methylpyrrolidone or dimethyl sulfoxide, in particular in tetrahydrofuran, with the aid of a metal such as lithium, sodium, potassium, magnesium or zinc, the latter being preferred, at 0° C. to the boiling point of the solvent, preferably at 40° to 100° C., with or without additional treatment with ultrasound.

Compounds of the formula IV in which $R^6$ denotes the —NR$^7$R$^8$ radical, and $R^1$, $R^2$, $R^3$, $R^4$, $R^5$, X, m, n and s are as defined in formula I are obtained from corresponding compounds of the formula IV in which $R^6$ denotes hydroxyl, through reaction with compounds of the formula V

in which $R^7$ and $R^8$ are as defined in formula I. A procedure analogous to the amide-linking processes which are customary in peptide chemistry, as described, for example, in Houben-Weyl, Volume 15/2, pages 1–364, in Bodanszky, "Principles and Practice in Peptide Synthesis", Berlin, 1984 and in U.S. Pat. Nos. 4,331,592 and 4,426,325, in preferably carried out, the reaction being carried out in an organic solvent such as DMF, CH$_2$Cl$_2$ or DMA, in the presence of coupling auxiliaries, such as carbodiimides (e.g. dicyclohexylcarbodiimide), diphenylphosphoryl azide, alkanephosphoric anhydrides, dialkylphosphinic anhydrides or N,N-succinimidyl carbonates in a solvent such as CH$_3$CN. The compounds of the formula IV can be converted into active esters (e.g. using 1-hydroxybenzotriazole), mixed anhydrides (e.g. using chloroformates), azides or carbodiimide derivatives, and are thus activated (cf. Schröder, Lübke, The Peptides, Volume 1, N.Y. 1965, pages 76–136). The reaction is preferably carried out between −20° C. and the boiling point of the reaction mixture.

In addition, in order to prepare compounds of the formula IV in which R$^6$ represents —NR$^7$R$^8$ and the other radicals and variables are as defined in formula I, corresponding compounds of the formula IV in which R$^6$ represents (C$_1$–C$_6$)-alkoxyphenoxy or (C$_7$–C$_{13}$)-aralkyloxy can be reacted with compounds of the formula V defined above in a suitable organic solvent, such as a lower alcohol, dimethylformamide or dimethyl sulfoxide, preferably in ethanol, at 20° C. to the boiling point of the reaction mixture, preferably at 40°–80° C.

Compounds of the formula II are either known from the literature or can be prepared analogously to processes which are known from the literature; some representatives are described, for example, in European patent application Nos. EP-A-172,458 and EP-A-201,742 and in Japanese patent application No. 1183–297, and also in Life Sci. 33, 2149 (1983).

The compounds of the formula I according to the invention are inhibitors of prolyl-endopeptidase (EC 3.4.21.26). It is known that this enzyme degrades neuropeptides such as substance P, neurotensin, LHRH, TRH, vasopressin and angiotensin II (Life Sci. 33, 2149 (1983)). These neuropeptides are associated with important functions in the central nervous system (CNS). By inhibiting their degradation by inhibiting prolyl-endopeptidase, various types of action, in particular antiamnestic, antipsychotic, anxiolytic and antidepressive actions, are initiated in the CNS by compounds of the formula I.

Compounds of the formula I are therefore suitable for treatment of various diseases of the central nervous system, in particular as nootropics and antipsychotics in warm-blooded animals, preferably in humans. The compounds according to the invention can be administered intravenously, subcutaneously or perorally, alone or in combination with other CNS-active substances.

Depending on the type and severity of the disorder to be treated, the dosage is 0.0001–10 mg/kg/day, in particular 0.001–1 mg/kg/day. It may also be increased in severe cases since toxic properties have hitherto not been observed.

The compounds according to the invention can be administered orally or parenterally in appropriate pharmaceutical preparations. For an oral form of administration, the active compounds are mixed with the additives which are conventional for this, such as excipients, stabilizers or inert diluents, and converted into suitable forms of administration by conventional methods, such as tablets, coated tablets, suppositories, aqueous, alcoholic or oil suspensions, or aqueous, alcoholic or oil solutions. Inert excipients which can be used are, for example, gum arabic, magnesium carbonate, potassium phosphate, lactose, glucose or starch, in particular maize starch. Formulation can take place here both as dry and moist granules. Possible oily excipients or solvents are, for example, vegetable and animal oils, such as sunflower oil or cod-liver oil.

For subcutaneous or intravenous administration, the active compounds or their physiologically acceptable salts, are brought into solution, suspension or emulsion, if desired using the substances which are conventional for this purpose, such as solubilizers, emulsifiers or further auxiliaries. Suitable solvents for the novel active compounds and the corresponding physiologically acceptable salts are, for example: water, physiological saline solutions or alcohols, for example ethanol, propanediol or glycerol, furthermore also sugar solutions such as glucose or mannitol solutions, or alternatively a mixture of the various solvents mentioned.

The following examples are intended to illustrate the present invention without representing a limitation.

EXAMPLE 1

Methyl 3-[N-(N-benzyloxycarbonyl-S-prolyl)-pyrrolidin-2-S-yl]-3-oxo-2,2-difluoropropionate (a) Methyl 3-[N-(N-benzyloxycarbonyl-S-prolyl)-pyrrolidin-2-S-yl]-3-hydroxy-2,2-difluoropropionate 1.2 g of zinc powder are heated to boiling in 30 ml of tetrahydrofuran with 3.75 g of methyl bromodifluoroacetate. 5 g of N-benzyloxy carbonyl-S-propyl-S-prolinal are subsequently added, and the mixture is heated for a further 15 minutes. After cooling, the mixture is worked up using 0.5N hydrochloric acid/acetic acid.

Chromatography on silica gel using ethyl acetate/cyclohexane (3:1) as eluent gives 5.1 g of the title compound, melting point 119°–120° C., $[\alpha]_D^{22} = -53.9°$ (c=0.232, CH$_2$Cl$_2$).

(b) Methyl 3-[N-(N-benzyloxycarbonyl-S-prolyl)-pyrrolidin-2-S-yl]-3-oxo-2,2-difluoropropionate 0.12 ml of dimethyl sulfoxide is added to 70 μl of oxalyl chloride in 10 ml of dichloromethane at −78° C. 0.32 g of the compound from Example 1(a) is added after 2 minutes, and 0.78 ml of triethylamine after a further 5 minutes. After warming to room temperature, the mixture is washed with 0.1N hydrochloric acid, aqueous 1M sodium hydrogen carbonate solution and saturated aqueous sodium chloride solution, dried using Na$_2$SO$_4$ and evaporated.

After chromatography on silica gel using ethyl acetate/cyclohexane (3:1), 0.17 g of the title compound is obtained as an oil.

$^1$H NMR (CDCl$_3$), δ=7.4–7.2 (m, 5H); 5.2–4.7 (m, 3H); 4.55–4.3 (m, 1H); 3.92–3,88 (2s, 3H); 3.95–3.8 (m 1H) 3.7–3.3 (m 4H); 2.3–1.5 (m, 7H) ppm.

EXAMPLE 2

N-Benzyl-3-[N-(N-benzyloxycarbonyl-S-prolyl)-pyrrolidin-2-S-yl]-3-oxo-2,2-difluoropropionamide (a) N-Benzyl-3-[N-(N-benzyloxycarbonyl-S-prolyl)-pyrrolidin-2-S-yl]-3-hydroxy-2,2-difluoropropionamide 0.308 g of the compound from Example 1(a) is refluxed for 4 hours under nitrogen with 0.3 ml of benzylamine in 10 ml of absolute ethanol. After evaporation, the residue is chromatographed on silica gel using ethyl acetate/cyclohexane (3:1). 0.25 g of the title compound, melting point 135° C., is obtained.

(b)
N-Benzyl-3-[N-(N-benzyloxycarbonyl-S-prolyl)-pyrrolidin-2-S-yl]-3-oxo-2,2-difluoropropionamide The compound from Example 2(a) (0.93 g) is oxidized analogously to the process specified in Example 1(b) using 0.19 ml of oxalyl chloride and 0.3 ml of DMSO in 5 ml of dichloromethane. After chromatography on silica gel using ethyl acetate/cyclohexane (3:1), 0.335 g of the title compound is obtained as an oil.

$^1$H NMR (CDCl$_3$): δ=7.6 (s,1H); 7.4–7.2 (m,10H); 5.2–4.9 (m,3H); 4.7–4.3 (m,4H); 3.95–3.5 (m,1H); 3.5–3.3 (m,3H); 2.4–1.7 (m,7H) ppm.

EXAMPLE 3

Methyl 3-[N-[4-(4-methoxyphenyl)-butyryl]-pyrrolidin-2-S-yl]-3-oxo-2,2-difluoropropionate (a) Methyl 3-[N-[4-(4-methoxyphenyl)-butyryl]-pyrrolidin-2-S-yl]-3-hydroxy-2,2-difluoropropionate Analogously to the process specified in Example 1(a), 6.2 g of the title compound are obtained as an oil, after chromatography on silica gel (ethyl acetate/cyclohexane 2:1), from 5.4 g of methyl bromodifluoroacetate and 6 g of 4-(4-methoxyphenylbutyryl)-S-prolinal using 1.7 g of zinc powder.

$^1$H NMR (CDCl$_3$): δ=7.2–6.7 (AB system, 4H); 4.7–4.2 (m,1H); 4.0–3.5 (m,1H); 3.9–3.8 (2s,3H); 3.6–3.1 (m,2H); 2.6 (t,2H); 2.4–1.6 (m,8H) ppm.

(b) Methyl 3-[N-[4-(4-methoxyphenyl)butyryl]-pyrrolidin-2-S-yl]-3-oxo-2,2-difluoropropionate Analogously to the procedure specified in Example 1(b), 0.54 g of the title compound is obtained as an oil from 0.8 g of the compound from Example 3(a); $[α]_D^{23}$=+55.3° (c=0.66, (CH$_2$Cl$_2$))

$^1$H NMR (CDCl$_3$): δ=7.2–6.6 (AB system,4H); 4.92 (t,1H); 3.97+3.8 (2s,3H); 3.6–3.3 (m,2H); 2.6 (t,2H); 2.4–1.7 (m,8H) ppm.

Analogously to the procedure specified in Example 2(a), the following were prepared from methyl 3-[N-[4-(4-methoxyphenyl)-butyryl]-pyrrolidin-2-S-yl]-3-hydroxy-2,2-difluoropropionate and the appropriate amines:

EXAMPLE 4

N-Benzyl-3-[N-[4-(4-methoxyphenyl)-butyrylpyrrolidin-2-S-yl]-3-hydroxy-2,2-difluoropropionamide 2 isomers were obtained in the ratio 8.5:1 and were separated by chromatography on SiO$_2$ (eluent ethyl acetate/cyclohexane=1:1).

Isomer 1: Oil, $[α]_D^{23}$= −34° (c=0.3, CH$_2$Cl$_2$). $^1$H NMR (CDCl$_3$): δ=7.3 (s,5H); 7.2–6.6 (AB system,4H); 4.6–4.4 (m,3H); 4.3–3.3 (m,3H); 3.8 (s,3H); 2.63 (t,2H); 2.4–1.8 (m,8H) ppm.

Isomer 2: Oil, $[α]_D^{23}$= −23.4° (c=0.124, CH$_2$Cl$_2$).
$^1$NMR (CDCl$_3$): δ=7.3 (s,5H); 7.2–6.6 (AB system,4H); 4.6–4.2 (m,3H); 3.8 (s,3H); 3.6–3.0 (m,3H); 2.63 (t,2H); 2.5–1.7 (m,8H) ppm.

EXAMPLE 5

N-(2-phenylethyl)-3-[N-[4-(4-methoxyphenyl)-butyryl]-pyrrolidin-2-S-yl]-3-hydroxy-2,2-difluoropropionamide 2 isomers were obtained in the ratio 7.8:1 and were separated by chromatography on SiO$_2$ (eluent ethyl acetate/cyclohexane=1:1).

Isomer 1: Oil, $[α]_D^{23}$= −40.9° (c=0.2, CH$_2$Cl$_2$).
$^1$H NMR (CDCl$_3$): δ=7.2 (s,5H); 7.2–6.7 (AB system,4H); 6.5 (s,1H); 4.6–4.3 (m,1H); 4.2–3.2 (m,5H); 3.8 (s,3H); 3.0–1.6 (m,12H) ppm.

Isomer 2: Oil, $[α]_D^{23}$= −22.6° (=0.112, CH$_2$Cl$_2$).
$^1$H NMR (CDCl$_3$): δ=7.2 (s,5H): 7.2–6.7 (AB system,4H); 4.6–4.0 (m,2H); 3.8 (s,3H); 3.7–3.1 (m,4H); 2.82 (t,2H); 2.6 (t,2H); 2.4–1.7 (m,10H) ppm.

EXAMPLE 6

N-(3-dimethylaminopropyl)-3-[N-[4-(4-methoxyphenyl)-butyryl]-pyrrolidin-2-S-yl]-3-hydroxy-2,2-difluoropropionamide $^1$H NMR (CDCl$_3$): δ=8.4 (S,1H); 7.2–6.6 (AB system,4H); 4.7–4.4 (m,1H); 4.3–3.6 (m,1H); 3.8 (s,3H); 3.6–3.3 (m,6H); 2.8–1.5 (m,12H); 2.25 (s,6H) ppm.

EXAMPLE 7

N-pyrrolidinyl-3-[N-[4-(4-methoxyphenyl)-butyryl]-pyrrolidin-2-S-yl]-3-hydroxy-2,2-difluoropropionamide
Oil $^1$H NMR (CDCl$_3$): δ=7.2–6.6 (AB system,4H); 5.9 (dd,1H); 4.7–4.4 (m,1H); 4.2–3.2 (m,7H); 3.8 (s,3H); 2.6 (t, 2H); 2.4–1.5 (m, 12H) ppm.

EXAMPLE 8

N-(2-picolyl)-3-[N-[4-(4-methoxyphenyl)-butyryl]-pyrrolidin-2-S-yl]-3-hydroxy-2,2-difluoropropionamide 2 isomers formed (ratio about 8:1), and the less polar isomer was separated off alone by column chromatography (eluent ethyl acetate), oil.
$[α]_D^{22}$= −35.5° (c=0.29, CH$_2$Cl$_2$).

$^1$H NMR (CDCl$_3$): δ=8.57 (d,1H); 7.7 (dt,2H); 7.32 (d,1H); 7.3–7.2 (m,1H); 7.1 (d,2H); 6.83 (d,2H); 6.0 (s,1H); 4.8–4.5 (m,3H); 4.05–3.9 (m,1H); 3.8 (s,3H); 3.4 (m,2H); 2.6 (t,2H); 2.4 (t,2H); 2.2–1.85 (m,6H) ppm.

EXAMPLE 9

N-benzyl-3-[N-[4-(4-methoxyphenyl)-butyryl]-pyrrolidin-2-S-yl]-2,2-difluoro-3-oxopropionamide 0.78 g of the compound from Example 4 (both isomers) are oxidized by the process specified in Example 1(b). 0.7 g of the title compound is obtained as an oil.

$[α]_D^{22}$= +8.3° (c=0.444, CH$_2$Cl$_2$).
$^1$H NMR (CDCl$_3$): δ=7.6 (s,1H); 7.3 (s,1H); 7.2–6.7 (AB system,4H); 4.98 (t,3H); 4.6–4.3 (AB system,2H); 3.8 (s,3H); 3.6–3.3 (m,2H); 2.55 (t,3H); 2.4–1.7 (m,8H) ppm.

EXAMPLE 10

N-(2-phenylethyl)-3-[N-[4-(4-methoxyphenyl)-butyryl]-pyrrolidin-2-S-yl]-2,2-difluoro-3-oxopropionamide 0.83 g of the compound from Example 5 (both isomers) is oxidized by the process specified in Example 1(b). 0.78 g of the title compound is obtained as an oil.
$[α]_D^{23}$= +16.7° (c=0.86, CH$_2$Cl$_2$).

¹H NMR (CDCl₃): δ=7.2 (s,5H); 7.2–6.7 (AB system,4H); 4.9 (t,1H); 3.8 (s,3H); 3.6–3.3 (m,4H); 2.86 (t,2H); 2.6 (t,2H); 2.4–1.3 (m,10H) ppm.

EXAMPLE 11

N-(3-dimethylaminopropyl)-3-[N-[4-(4-methoxyphenyl)-butyryl]-pyrrolidin-2-S-yl]-2,2-difluoro-3-oxopropionamide 0.66 g of the compound from Example 6 is oxidized analogously to the process described in Example 1(b). 0.19 g of the title compound is obtained as an oil after chromatography on SiO₂ using CH₂Cl₂/CH₃OH (8:2).

¹H NMR (CDCl₃): δ=9.0 (s,1H); 7.1 (d,2H); 6.83 (d,2H); 5.0 (dd,1H); 3.8 (s,3H); 3.6–3.4 (m,3H); 2.6 (t,2H); 2.4 (t,2H); 2.33 (s,6H); 2.1–1.6 (m,8H) ppm.

EXAMPLE 12

N-pyrrolidinyl-3-[N-[4-(4-methoxyphenyl)-butyryl]-pyrrolidin-2-S-yl]-2,2-difluoro-3-oxopropionamide 0.46 g of the compound from Example 7 is oxidized analogously to the process described in Example 1(b). 0.35 g of the title compound is obtained as crystals of melting point 94°–95° C.

$[\alpha]_D^{22} = +41.4°$ (c=0.294, CH₂Cl₂).

EXAMPLE 13

N-(2-picolyl)-3-[N-[4-(4-methoxyphenyl)-butyryl]-pyrrolidin-2-S-yl]-2,2-difluoro-3-oxopropionamide 0.81 g of the compound from Example 8 is oxidized analogously to the process described in Example 1(b). 0.8 g of the title compound is obtained as an oil.

$[\alpha]_D^{22} = +10°$ (c=0.412, CH₂Cl₂).

¹H NMR (CDCl₃): δ=8.55 (m,1H); 8.3–8.0 (m,1H); 7.7–7.1 (m,2H); 7.2–6.3 (AB system,4H); 6.05 (t,1H); 4.65 (AB system,2H); 3.8 (s,3H); 3.5 (t,2H); 2.55 (t,2H); 2.5–1.6 (m,8H) ppm.

EXAMPLE 14

Methyl 3-[N-(3,3-diphenylpropionyl)-pyrrolidin-2-S-yl]-2,2-difluoro-3-oxopropionate (a) Methyl 3-[N-(3,3-diphenylpropionyl)-pyrrolidin-2-S-yl]-2,2-difluoro-3-hydroxypropionate Analogously to the process described in Example 1(a), 6.14 g of N-(3,3-diphenylpropionyl)-S-prolinal are reacted with 4.95 g of methyl bromodifluoroacetate and 1.55 g of zinc. After column chromatography on SiO₂ using ethyl acetate/cyclohexane (1:1) as eluent, 6.45 g of the title compound are obtained as an oil.

¹H NMR (CDCl₃): δ=7.2 (s,10H); 5.9 (dd,1H); 4.6 (t,1H); 4.6–4.2 (m,1H); 4.1–3.5 (m,1H); 3.87 (s,3H); 3.25 (t,2H); 3.0 (d,2H); 2.0–1.6 (m,4H) ppm.

(b) Methyl 3-[N-(3,3-diphenylpropionyl)-pyrrolidin-2-S-yl]-2,2-difluoro-3-oxopropionate 0.8 g of the compound from (a) is oxidized analogously to the process described in Example 1(b). 0.65 g of the title compound is obtained as an oil.

$[\alpha]_D^{23} = +30.5°$ (c=0.57, CH₂Cl₂).

¹H NMR (CDCl₃): δ=7.2 (s,10H); 4.83 (t,1H); 4.63 (t,1H); 3.83 (s,3H); 3.6–3.2 (m,2H); 3.0 (d,2H); 2.3–1.8 (m,6H) ppm.

The following were prepared analogously to the procedure specified in Example 2(a) in each case from 0.8 g of methyl 3-[N-(3,3-diphenylpropionyl)-pyrrolidin-2-S-yl]-2,2-difluoro-3-hydroxypropionate and 4 equivalents of the particular amine:

EXAMPLE 15

N-benzyl-3-[N-(3,3-diphenylpropionyl)-pyrrolidin-2-S-yl]-2,2-difluoro-3-hydroxypropionamide Oil: 0.81 g ¹H NMR (CDCl₃): δ=7.3 (s,5H); 7.2 (s,10H); 5.95 (dd,1H); 4.8–4.3 (m,3H); 4.3–3.6 (m,1H); 3.4 (t,2H); 3.05 (d,2H); 2.2–1.5 (m,4H) ppm.

EXAMPLE 16

N-(2-picolyl)-3-[N-(3,3-diphenylpropionyl)-pyrrolidin-2-S-yl]-2,2-difluoro-3-hydroxypropionamide Oil: 0.88 g ¹H NMR (CDCl₃): δ=8.55 (d,1H); 7.73–7.65 (m,2H); 7.35–7.15 (m,11H); 4.7–4.3 (m,4H); 3.9–3.8 (ddd,1H); 3.3 (t,2H); 3.15–3.0 (m,2H); 2.0–1.7 (m,4H) ppm.

EXAMPLE 17

N-benzyl-3-[N-(3,3-diphenylpropionyl)-pyrrolidin-2-S-yl]-2,2-difluoro-3-oxopropionamide 0.81 g of the compound from Example 15 is oxidized by the process described in Example 1(b). 0.67 g of the title compound is obtained as an oil.

$[\alpha]_D^{22} = -3.5°$ (c=0.36, CH₂Cl₂).

¹H NMR (CDCl₃): δ=7.4–7.0 (m,15H); 5.0–4.5 (m,1H); 4.5 (AB system,2H); 3.6–3.2 (m,2H); 3.0 (d,2H); 2.4–1.6 (m,4H) ppm.

EXAMPLE 18

N-(2-picolyl)-3-[N-(3,3-diphenylpropionyl)-pyrrolidin-2-S-yl]-2,2-difluoro-3-oxopropionamide 0.88 g of the compound from Example 1(b) is oxidized by the process described in Example 1(b). 0.58 g of the title compound is obtained as an oil.

$[\alpha]_D^{22} = -4.4°$ (c=9.476, CH₂Cl₂).

¹H NMR (CDCl₃): δ=8.55 (d,1H); 8.3–7.6 (m,2H); 7.5–7.0 (m,11H); 5.1–4.5 (m,5H); 3.6–3.3 (m,2H); 3.0 (d,2H); 2.4–1.7 (m,4H) ppm.

EXAMPLE 20

Methyl 3-[N-[N-(4-phenylbutyryl)-S-prolyl]-pyrrolidin-2-S-yl]-3-oxo-2,2-difluoropropionate (a) Methyl 3-[N-[N-(4-phenylbutyryl)-S-prolyl]-pyrrolidin-2-S-yl]-3-hydroxy-2,2-difluoropropionate Analogously to the process described in Example 1(a), 2.3 g of N-[N-(4-phenylbutyryl)-S-prolyl]-S-prolinal are reacted with 0.5 g of zinc and 1.4 g of methyl bromodifluoroacetate. After chromatography on SiO₂ using ethyl acetate/methanol (40:1) as eluent, 1.65 g of the title compound are obtained as an oil.

¹H NMR (CDCl₃): δ=7.3–7.15 (m,5H); 5.0–4.2 (m,2H); 4.2–3.9 (m,2H); 3.9 (s,3H); 3.8–2.9 (m,3H); 2.7 (m,2H); 2.4–1.8 (m,12H) ppm.

(b) Methyl 3-[N-[N-(4-phenylbutyryl)-S-prolyl]-pyrrolidin-2-S-yl]-3-oxo-2,2-difluoropropionate 0.55 g of the compound from (a) is oxidized analogously to the process specified in Example 1(b). After chromatography (SiO₂, ethyl acetate), 0.26 g of the title compound is obtained as an oil.

$[\alpha]_D^{22}$=21.7° (c=2.2, CH₂Cl₂).

¹H NMR (CDCl₃): δ=7.3–7.1 (m,5H); 5.1–4.9 (m,1H); 4.75–4.6 (m,1H); 4.0–3.8 (m,1H); 3.9 (s,3H); 3.7–3.3 (m,4H); 2.7 (t,2H); 2.9–1.8 (m,12H); ppm.

EXAMPLE 21

N-benzyl-3-[N-[N-(4-phenylbutyryl)-S-prolyl]-pyrrolidin-2-S-yl]-3-oxo-2,2-difluoropropionamide (a)

N-benzyl-3-[N-[N-(4-phenylbutyryl)-S-prolyl]-pyrrolidin-2-S-yl]-3-hydroxy-2,2-difluoropropionamide 0.55 g of the compound from Example 20(a) is reacted analogously to the process described in Example 2(a) with 0.6 ml of benzylamine. 0.5 g of the title compound is obtained as an oil.

¹H NMR (CDCl₃): δ=7.4–7.1 (m,10H); 6.9–6.7 (m,1H); 4.9–4.3 (m,4H); 4.1–3.8 (m,2H); 3.7–2.9 (m,3H); 2.7(t,2H); 2.4–1.8 (m,12H); ppm.

(b)

N-benzyl-3-[N-[N-(4-phenylbutyryl)-S-prolyl]-pyrrolidin-2-S-yl]-3-oxo-2,2-difluoropropionamide 0.5 g of the compound from (a) is oxidized by the process specified in Example 1(b). 0.38 g of the title compound is obtained as an oil.

$[\alpha]_D^{22}$=−29.3° (c=3.1, CH₂Cl₂).

¹H NMR (CDCl₃): δ=7.7 (s,1H); 7.4–7.1 (m,10H); 5.05 (dd,1H); 4.65–4.3 (m,3H); 3.95 (m,1H); 3.6 (m,1H); 3.5–3.3 (m,2H); 2.67 (t,2H); 2.4–1.8 (m,12H); ppm.

EXAMPLE 22

Methyl 3-[N-[N-(3,3-diphenylpropionyl)-S-prolyl]-pyrrolidin-2-S-yl]-3-oxo-2,2-difluoropropionate (a) Methyl 3-[N-[N-(3,3-diphenylpropionyl)-S-prolyl]-pyrrolidin-2-S-yl]-3-hydroxy-2,2-difluoropropionate 17.5 g of N-[N-(3,3-diphenylpropionyl)-S-prolyl]-S-prolinal are reacted with 3.4 g of zinc and 10.7 g of methyl bromodifluoroacetate analogously to the process described in Example 1(a). 10.5 g of the title compound are obtained as an oil.

¹H NMR (CDCl₃): δ=7.3 (s,10H); 4.8–3.2 (m,7H); 3.9 (s,3H); 3.05 (d,2H); 2.4–1.6 (m,8H) ppm.

(b) Methyl 3-[N-[N-(3,3-diphenylpropionyl)-S-prolyl]-pyrrolidin-2-S-yl]-3-oxo-2,2-difluoropropionate 0.6 g of the compound from (a) is oxidized analogously to the process specified in Example 1(b). After chromatography (SiO₂, ethyl acetate/cyclohexane 2:1), 0.31 g of the title compound is obtained as an oil.

$[\alpha]_D^{24}$=−33.8° (c=0.408, CH₂Cl₂).

¹H NMR (CDCl₃): δ=7.3–7.1 (m,10H); 5.0 (dd,1H); 4.65 (dd,1H); 4.55 (dd,1H); 3.9 (m,4H); 3.3 (m,1H); 3.1 (m,2H); 3.05 (ddd,2H); 2.3–1.7 (m,8H) ppm.

The compounds of the formula I a listed in the Table below were attained analogously to the process steps specified in Example 2 using suitable starting materials.

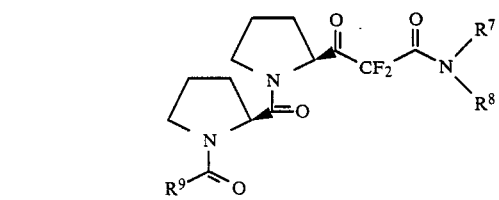

Ia

| Ex. No. | R⁷ | R⁸ | R⁹ | $[\alpha]_D^{24}$(CH₂Cl₂) | ¹H NMR (CDCl₃); δ Values (ppm) |
|---|---|---|---|---|---|
| 23 | H | —(CH₂)₂—C₆H₅ | C₆H₅—CH₂—O— | −36.7° (c = 0.572) | 7.38 (s,5H); 5.2 (s.2H); 5.1–3.3 (m.8H); 2.8 (t,2H); 2.4–1.5 (m,8H). |
| 24 | H | —(CH₂)₃—C₆H₅ | C₆H₅—CH₂—O— | −33.6° (c = 0.438) | 7.3 (s,5H); 5.2 (s,2H); 5.1–3.2 (m,8H); 2.6 (t,2H); 2.4–1.6 (m,10H). |
| 25 | H | —CH₂-(3-pyridyl) | C₆H₅—CH₂—O— | −44.3° (c = 0.56) | 8.55 (d,1H); 8.02 (s,1H); 7.6 (q,1H); 7.4–7.15 (m,6H); 5.2–4.3 (m,8H); 3.7–3.3 (m,4H); 2.4–1.7 (m,8H). |
| 26 | H | —CH(CH₃)—C₆H₅ | C₆H₅—CH₂—O— | −7.6° (c = 0.434) | 7.7–7.5 (2d,1H); 7.4–7.2 (m,5H); 5.2–4.9 (m,2H); 5.1–4.35 (m,2H); 3.95–3.55 (m,1H); 3.6–3.3 (m,4H); 2.4–1.7 (m,8H); 1.55 (2d,3H). |

-continued

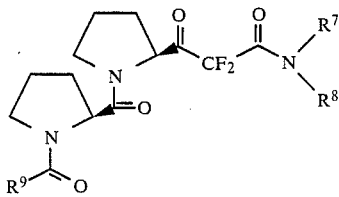

Ia

| Ex. No. | R⁷ | R⁸ | R⁹ | $[\alpha]_D^{24}(CH_2Cl_2)$ | ¹H NMR (CDCl₃); δ Values (ppm) |
|---|---|---|---|---|---|
| 27 | H | CH₃<br>—CH—C₆H₅ | C₆H₅—CH₂—O— | −58°<br>(c = 0.512) | 7.7 (m,1H); 7.4–7.2 (m,5H); 5.2–4.9 (m,2H); 5.1–4.6 (m,2H); 3.9–3.3 (m,5H); 2.3–1.8 (m,8H); 1.5 (2d,3H). |
| 28 | H | —(CH₂)₃—N(CH₃)₂ | C₆H₅—CH₂—O— | −23°<br>(c = 0.392) | 9.0 (m,1H); 7.4 (s,5H); 5.2–4.9 (m,2H); 5.1–4.6 (m,2H); 3.8–3.2 (m,6H); 2.6–1.6 (m,12H); 2.25 (s,6H). |
| 29 | H | —(CH₂)₂—C₆H₅ | (C₆H₅)₂CH—CH₂— | −51.1°<br>(c = 0.47) | 7.4–7.1 (m,10H); 5.0–4.5 (m,2H); 3.9–3.3 (2m,2H); 3.7–3.5 (m,4H); 3.15–2.9 (m,2H); 2.85 (t,2H); 2.3–1.7 (m,10H). |
| 30 | H | —CH₂-(2-pyridyl) | (C₆H₅)₂CH—CH₂— | −60.2°<br>(c = 0.382) | 8.5 (d,1H); 8.1 (m,1H); 7.65 (dt,1H); 7.3–7.1 (m,11H); 5.1 (m,1H); 4.7–4.5 (m,5H); 3.9 (m,1H); 3.4–3.2 (m,2H); 3.3 (m,1H); 3.0 (m,2H); 2.3–1.7 (m,8H). |
| 31 | H | —CH₂—C₆H₅ | (C₆H₅)CH—CH₂ | −47.7°<br>(c = 0.342) | 7.7 (m,1H); 7.4–7.1 (m,10H); 5.0 (m,1H); 4.7–4.3 (m,3H); 3.9–2.8 (m,4H); 2.3–1.7 (m,8H). |
| 32 | H | CH₃<br>—CH—C₆H₅ | (C₆H₅)₂CH—CH₂— | −29.2°<br>(c = 0.048) | 7.7 (d,1H); 7.4–7.1 (m,10H); 5.15 (m,1H); 5.0 (m,1H); 4.65 (m,1H); 4.55 (m,1H); 3.9–2.9 (m,4H); 2.3–1.7 (m,8H). |
| 33 | H | —CH₂-(2-pyridyl) | CH₃O— | —(CH₂)₃—C₆H₄—<br>43.2°<br>(c = 0.412) | 8.5 (d,1H); 8.1 (m,1H); 7.65 (dt,1H); 7.25 (m,2H); 7.1–6.7 (m,4H); 5.1 (m,1H); 4.65 (m,2H); 4.0–3.3 (m,3H); 3.8 (s,3H); 2.6 (t,2H); 2.4–1.8 (m,12H). |
| 34 | —(CH₂)₄— | | C₆H₅—CH₂—O— | −11.9°<br>(c = 0.404) | 7.4–7.2 (m,5H); 5.2–4.9 (m,2H); 4.8–3.8 (m,2H); 3.7–3.3 (m,8H); 2.4–1.7 (m,12H). |
| 35 | —(CH₂)₂—O—(CH₂)₂— | | C₆H₅—CH₂—O— | −20.7°<br>(c = 0.434) | 7.4–7.2 (m,5H); 5.2–4.9 (m,2H); 5.1–4.35 (m,2H); 3.9–3.3 (m,12H); 2.3–1.8 (m,8H). |
| 36 | —(CH₂)₂—N(CH₃)—(CH₂)₂— | | C₆H₅—CH₂—O— | −27.2°<br>(c = 0.492) | 7.4–7.2 (m,5H); 5.2–4.9 (m,2H); |

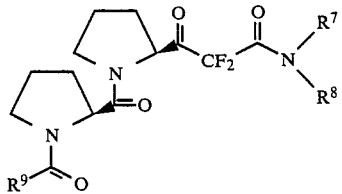

| Ex. No. | $R^7$ | $R^8$ | $R^9$ | $[\alpha]_D^{24}(CH_2Cl_2)$ | $^1H$ NMR (CDCl$_3$); δ Values (ppm) |
|---|---|---|---|---|---|
| | | | | | 5.2–4.9 (m,2H); 5.1–4.6 (m,2H); 3.95–3.3 (m,8H); 2.6–1.8 (m,12H); 2.3 (2s,3H). |
| 37 | | (CH$_2$)$_2$ N—(CH$_2$)$_2$—⟨aryl with OCH$_3$, OCH$_3$, OCH$_3$⟩ (CH$_2$)$_2$ | C$_6$H$_5$—CH$_2$—O— | −21.7° (c = 0.552) | 7.4–7.2 (m,5H); 6.42–6.4 (2s,2H); 5.2–4.9 (m,2H); 5.1–4.6 (m,2H); 3.85, 3.83, 3,80 (3s,9H); 3.9–3.3 (m,8H); 2.8–1.8 (m,16H). |

We claim:

1. A compound of the formula I

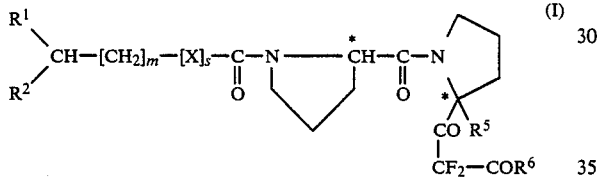

in which $R^1$ denotes hydrogen; (C$_1$–C$_6$)-alkyl; or (C$_6$–C$_{12}$)-aryl, said aryl being optionally substituted by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or one (C$_1$ or C$_2$)-alkylenedioxy;

$R^2$ denotes hydrogen; (C$_1$–C$_6$)-alkyl; (C$_6$–C$_{12}$)-aryl; (C$_6$–C$_{12}$)-aryloxy; (C$_7$–C$_{13}$)-aroyl; hydroxyl or (C$_1$–C$_4$)-alkoxy, where said aryl, aryloxy and aroyl are in each case optionally substituted by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or by one (C$_1$ or C$_2$)-alkylenedioxy; or $R^1$ and $R^2$ together represent benzylidene in which the phenyl ring is optionally substituted by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or by one (C$_1$ or C$_2$)-alkylenedioxy;

$R^5$ denotes hydrogen; (C$_1$–C$_6$)-alkyl; (C$_6$–C$_{12}$)-aryl-(C$_1$–C$_5$)-alkyl which is optionally substituted in the aryl part by one, two or three identical or different radicals selected from (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or by one (C$_1$ or C$_2$)-alkylenedioxy;

$R^6$ denotes (C$_1$–C$_8$)-alkyl; (C$_6$–C$_{12}$)-aryl; (C$_6$–C$_{12}$)-aryl-(C$_1$–C$_6$)-alkyl; hydroxyl; (C$_1$–C$_8$)-alkoxy; (C$_6$–C$_{12}$)-aryloxy or (C$_6$–C$_{12}$)-aryl-(C$_1$–C$_6$)-alkoxy, where said aryl, aralkyl, aryloxy and arylalkoxy groups are in each case optionally substituted in the aryl part by one, two or three identical or different radicals selected from (C$_1$–C$_4$)-alkyl, (C$_1$ or C$_2$)-alkoxy, halogen and nitro, or by one (C$_1$ or C$_2$)-alkylenedioxy; or $R^6$ represents a radical of the formula —NR$^7$R$^8$ in which $R^7$ and $R^8$ are identical or different and denote hydrogen; (C$_1$–C$_8$)-alkyl; (C$_4$–C$_{10}$)-cycloalkyl; (C$_1$–C$_4$)-alkyl-(C$_4$–C$_{10}$)-cycloalkyl; (C$_6$–C$_{12}$)-aryl; (C$_6$–C$_{12}$)-aryl-(C$_1$–C$_6$)-aryl; amino-(C$_1$–C$_8$)-alkyl; (C$_1$–C$_4$)-alkylamino-(C$_1$–C$_8$)-alkyl; di-(C$_1$–C$_4$)-alkylamino-(C$_1$–C$_8$)-alkyl; hydroxy-(C$_1$–C$_8$)-alkyl or (C$_1$–C$_4$)-alkoxy-(C$_1$–C$_8$)-alkyl, where said aryl and aralkyl groups are in each case optionally substituted in the aryl part by one, two or three identical or different radicals selected from (C$_1$–C$_4$)-alkyl, (C$_1$ or C$_2$)-alkoxy, (C$_1$–C$_4$)-alkylamino, di-(C$_1$–C$_4$)-alkylamino, halogen, hydroxyl and amino, or by one (C$_1$ or C$_2$)-alkylenedioxy;

X denotes oxygen; imino or N-(C$_1$–C$_8$)-alkylimino;

m is 0, 1, 2, 3, 4 or 5; and s is 0 or 1;

or a physiologically acceptable salt thereof.

2. A compound of the formula I as claimed in claim 1, in which $R^1$ and $R^2$ are identical or different and denote hydrogen; or phenyl, said phenyl being optionally substituted by one or two identical or different radicals selected from methyl, ethyl, methoxy, fluorine, chlorine, bromine, nitro, hydroxyl, amino, methylamino and dimethylamino, or by three methoxy, or by one methylenedioxy;

$R^5$ denotes hydrogen;

$R^6$ represents methoxy or a radical of the formula —NR$^7$R$^8$ in which $R^7$ and $R^8$ are identical or different and denote hydrogen; (C$_1$–C$_6$)-alkyl; (C$_5$–C$_8$)-cycloalkyl; (C$_1$ or C$_2$)-alkyl-(C$_5$–C$_8$)-cycloalkyl; phenyl; phenyl-(C$_1$–C$_4$)-alkyl; amino-(C$_1$–C$_4$)-alkyl; (C$_1$ or C$_2$)-alkylamino-(C$_1$–C$_4$)-alkyl; di-(C$_1$ or C$_2$)-alkylamino-(C$_1$–C$_4$)-alkyl; hydroxy-(C$_1$–C$_4$)-alkyl or (C$_1$ or C$_2$)-alkoxy-(C$_1$–C$_4$)-alkyl; and X denotes oxygen;
or a physiologically acceptable salt thereof.

3. A compound of the formula I as claimed in claim 1, in which
$R^1$ and $R^2$ are identical or different and denote hydrogen; phenyl; o-, m- or p-tolyl; o-, m- or p-chlorophenyl; o-, m- or p-fluorophenyl; o-, m- or p-methoxyphenyl or 2,3-, 2,4-, 2,5-, 2,6-, 3,4- or 3,5-dimethoxyphenyl;
$R^5$ denotes hydrogen;
$R^6$ denotes methoxy or a radical of the formula $-NR^7R^8$ in which
$R^7$ and $R^8$ are identical or different and denote hydrogen; $(C_1-C_6)$-alkyl; $(C_5-C_8)$-cycloalkyl; phenyl; phenyl-$(C_1-C_4)$-alkyl; amino-$(C_1-C_4)$-alkyl; methylamino-$(C_1-C_4)$-alkyl; dimethylamino-$(C_1-C_4)$-alkyl; hydroxy-$(C_1-C_4)$-alkyl or methoxy-$(C_1-C_4)$-alkyl; and
X denotes oxygen;
or a physiologically acceptable salt thereof.

4. A compound of the formula I as claimed in claim 1, in which
$R^2$ denotes hydrogen;
$R^5$ denotes hydrogen;
X denotes oxygen;
m is 0, 1 or 2;
or a physiologically acceptable salt thereof.

5. A compound of the formula I as claimed in claim 1, in which
$R^5$ denotes hydrogen; and
$R^7$ and $R^8$ are identical or different and denote hydrogen; $(C_1-C_6)$-alkyl; phenyl-$(C_1-C_4)$-alkyl; or dimethylamino-$(C_1-C_4)$-alkyl;
or a pharmaceutically acceptable salt thereof.

6. A compound of the formula I as claimed in claim 1, in which
$R^1$ and $R^2$ are identical or different and denote hydrogen, phenyl or p-methoxyphenyl;
$R^5$ denotes hydrogen;
$R^6$ denotes methoxy or a radical of the formula $-NR^7R^8$ in which
$R^7$ denotes hydrogen and $R^8$ denotes phenylmethyl, phenylethyl, phenylpropyl, dimethylaminopropyl or (1-methyl,1-phenyl)methyl;
X denotes oxygen;
m is 0, 1 or 2;
or a physiologically acceptable salt thereof.

7. A compound of the formula I as claimed in claim 1 in which
$R^1$ and $R^2$ are identical or different and denote hydrogen; $(C_1-C_6)$-alkyl; or $(C_6-C_{12})$-aryl, said aryl being optionally substituted by one, two or three identical or different radicals selected from $(C_1-C_4)$-alkyl, $(C_1-C_4)$-alkoxy, halogen, nitro, hydroxyl, amino, $(C_1-C_4)$-alkylamino and di-$(C_1-C_4)$-alkylamino, or one $(C_1$ or $C_2)$-alkylenedioxy;
$R^5$ denotes hydrogen; and
X denotes oxygen;
or a physiologically acceptable salt thereof.

8. The compound of claim 1 which is N-benzyl-3-[N-(N-benzyloxycarbonyl-S-prolyl)-pyrrolidin-2-S-yl]-3-oxo-2,2-difluoropropionamide.

9. The compound of claim 1 which is N-benzyl-3-[N-[N-(4-phenylbutyryl)-S-prolyl]-pyrrolidin-2-S-yl]-3-oxo-2,2-difluoropropionamide.

10. The compound of claim 1 which is N-(2-phenylethyl)-3-[N-(N-benzyloxycarbonyl-S-prolyl)-pyrrolidin-2-S-yl]-3-oxo-2,2-difluoropropionamide.

11. The compound of claim 1 which is N-(3-phenylpropyl)-3-[N-(N-benzyloxycarbonyl-S-prolyl)-pyrrolidin-2-S-yl]-3-oxo-2,2-difluoropropionamide.

12. The compound of claim 1 which is N-(1-S-phenylethyl)-3-[N-(N-benzyloxycarbonyl-S-prolyl)-pyrrolidin-2-S-yl]-3-oxo-2,2-difluoropropionamide.

13. The compound of claim 1 which is N-(1-R-phenylethyl)-3-[N-(N-benzyloxycarbonyl-S-prolyl)-pyrrolidin-2-S-yl]-3-oxo-2,2-difluoropropionamide.

14. The compound of claim 1 which is N-(2-phenylethyl)-3-[N-(N-benzhydrylmethylcarbonyl-S-prolyl)-pyrrolidin-2-S-yl]-3-oxo-2,2-difluoropropionamide.

15. The compound of claim 1 which is N-benzyl-3-[N-(N-benzhydrylmethylcarbonyl-S-prolyl)-pyrrolidin-2-S-yl]-3-oxo-2,2-difluoropropionamide.

16. The compound of claim 1 which is N-(1-R-phenylethyl)-3-[N-(N-benzhydrylmethylcarbonyl-S-prolyl)-pyrrolidin-2-S-yl]-3-oxo-2,2-difluoropropionamide.

17. A pharmaceutical composition comprising a compound of the formula I or a pharmaceutically acceptable salt thereof as claimed in claim 1 in an amount effective for treating at least one disease of the central nervous system, and a pharmaceutically acceptable carrier.

18. A pharmaceutical composition comprising a compound of the formula I or a pharmaceutically acceptable salt thereof as claimed in claim 1 in an amount effective for treating at least one disease of the central nervous system, wherein said compound or said salt is an inhibitor of prolylendopeptidase, and a pharmaceutically acceptable carrier.

19. A method of inhibiting prolyl-endopeptidase by administering a compound of formula I or a pharmaceutically acceptable salt thereof as claimed in claim 1 in an amount effective for treating at least one disease of the central nervous system.

* * * * *

UNITED STATES PATENT AND TRADEMARK OFFICE
CERTIFICATE OF CORRECTION

PATENT NO. : 4,912,128
DATED : March 27, 1990
INVENTOR(S) : Rainer HENNING et al.

It is certified that error appears in the above-identified patent and that said Letters Patent is hereby corrected as shown below:

In the Title Page

In item [75] Inventors, line 3, "Kronbert" should read --Kronberg/Taunus--.

In claim 1 at column 18, line 36, "aryl-$(C_1-C_6)$-aryl" should read --aryl-$(C_1-C_6)$-alkyl--.

Signed and Sealed this

Eighth Day of September, 1992

Attest:

DOUGLAS B. COMER

Attesting Officer     Acting Commissioner of Patents and Trademarks